(12) United States Patent
Nair et al.

(10) Patent No.: US 6,958,424 B1
(45) Date of Patent: Oct. 25, 2005

(54) PROCESS FOR FLUOROALKENES

(75) Inventors: Haridasan K. Nair, Williamsville, NY (US); Andrew J. Poss, Kenmore, NY (US)

(73) Assignee: Honeywell International Inc., Morristown, NJ (US)

(*) Notice: Subject to any disclaimer, the term of this patent is extended or adjusted under 35 U.S.C. 154(b) by 0 days.

(21) Appl. No.: 11/009,839

(22) Filed: Dec. 10, 2004

(51) Int. Cl.$^7$ ............................................ C07C 17/23
(52) U.S. Cl. ...................... 570/261; 570/101; 570/123
(58) Field of Search ................ 570/101, 123, 570/261

(56) References Cited

U.S. PATENT DOCUMENTS 4,220,608 A  9/1980  Feiring
5,986,151 A  11/1999  Van De Puy
6,673,976 B1  1/2004  Nair et al.

FOREIGN PATENT DOCUMENTS

DE     EP 0 396 974 A1 * 11/1990 .................. 570/261

* cited by examiner

Primary Examiner—Elvis O. Price
Assistant Examiner—Lansana Nyalley
(74) Attorney, Agent, or Firm—Deborah M. Chess

(57) ABSTRACT

Disclosed is a process for producing fluoroalkene of the formula $R_f$—CH=CH$_2$ from a fluorohaloalkene having the formula $R_f$—C(R$_1$)=C(R$_2$)H, wherein $R_f$ is fluorine or a substituted or unsubstituted $C_1$–$C_{20}$ straight or branched-chain fluorinated alkyl and $R_1$ and $R_2$ are independently H, Cl, Br, or I, provided that at least one of $R_1$ or $R_2$ is Cl, Br, or I by reacting the fluorohaloalkene with a reducing agent, preferably a formate salt in the presence of a catalyst.

37 Claims, 1 Drawing Sheet

PROCESS FOR FLUOROALKENES

FIELD OF THE INVENTION

The present invention relates to the preparation of fluoroalkenes. More particularly, the present invention relates to processes for conversion of certain fluorohaloalkenes to more desirable fluorinated products.

BACKGROUND OF THE INVENTION

In general, fluoroalkenes are very useful compounds having many applications. For example, fluorinated alkenes such as 3,3,3-trifluoropropene ($CF_3CH=CH_2$) are useful as monomers for the manufacture of polymers (for example, fluorosilicones) and starting materials in the production of fluorinated chemical intermediates such as trifluoropropene epoxide and 3,3,3-trifluoropropylbenzene. Fluorinated alkenes are also used as aerosol propellants and as refrigerants.

Fluorinated alkenes such as, for example, 3,3,3-trifluoropropene, however, typically are made in multi-step processes. For example, carbon tetrachloride ($CCl_4$) is typically added to ethylene to produce 1-chloro-3,3,3-trifluoropropane ($CCl_3CH_2CH_2Cl$). A. L. Henne, et al, J. Am. Chem. Soc., 72 (1950) 3369, for example, teaches that fluorination of the latter using a $CCl_3CH_2CH_2Cl$ liquid phase fluorination process, such as HF in conjunction with an antimony catalyst, provides 1-chloro-3,3,3-trifluoropropane ($CF_3CH_2CH_2Cl$) which is subsequently dehydrochlorinated to yield 3,3,3-trifluoropropene. Alternatively, German Patent 1 140 928 teaches that $CCl_3CH_2CH_2Cl$ can be fluorinated in a vapor phase process to yield 3,3,3-trifluoropropene.

U.S. Pat. No. 5,986,151 also describes a multi-step process for making 3,3,3-trifluoropropene. In U.S. Pat. No. 5,986,151, the first step of the process requires the dehydrofluorination of 1,1,1,3,3-pentafluoropropane ($CF_3CH_2CHF_2$; HFC-245fa) to 1,3,3,3-tetrafluoropropene ($CF_3CH=CHF$) (HFC 1234ze). In the next step, 1,3,3,3-tetrafluoropropene ($CF_3CH=CHF$) is reduced to 1,3,3,3-tetrafluoropropane ($CF_3CH_2CH_2F$) by reacting a stream of gaseous 1,3,3,3-tetrafluoropropene ($CF_3CH=CHF$) and hydrogen gas under catalytic conditions at suitable reaction temperatures. Finally, the 1,3,3,3-tetrafluoropropane ($CF_3CH_2CH_2F$) is dehydrofluorinated to yield 3,3,3-trifluoropropene.

Other methods for producing fluoroalkenes include the use of hazardous reagents. U.S. Pat. No. 6,211,421, for example, describes the preparation of 1,1,1-trifluoropropene by liquid phase fluorination of 1,1,3-trichloroprop-1-ene with HF. U.S. Pat. No. 4,582,921 describes the reaction of vinylbromide with in situ generated trifluoromethylorganometallic reagents to yield 3,3,3-trifluoropropene ($CF_3CH=CH_2$). U.S. Pat. No. 4,220,608 describes fluorination of $CCl_3CH_2CH_2Cl$ or $CCl_3CH=CCl_2$ with HF in the presence of an amine to yield 3,3,3-trifluoropropene ($CF_3CH=CH_2$). In yet another publication, Organometallics, 19(5), 944–946, 2000, 3,3,3-trifluoropropene ($CF_3CH=CH_2$) is obtained via thermal conversion of trifluoromethyl oxirane with only a 32% yield.

As can be seen from the above description, many prior processes involve the use and/or production of chlorinated alkenes. Applicants have come to appreciate, therefore, that many of these processes result in the generation of one or more unwanted waste streams containing chlorinated products. As is known, chlorinated compounds are generally considered to be problematic from an environmental standpoint. For example, chlorinated hydrocarbons are frequently identified with environmental problems such as ozone depletion and global warming. Heretofore, these unwanted waste streams typically were disposed of by incineration, which itself is frequently considered environmentally unfriendly as well as economically inefficient.

The above processes also generally suffer from other drawbacks. These include the use of expensive or hazardous starting materials and/or the use of reagents and/or starting materials that need to be prepared in multiple steps. Another drawback of many prior processes is that the conversion of starting materials to the desired product such as, for example, $CF_3CH=CH_2$, involves multiple steps that make such processes less cost effective than is desirable for many commercial purposes. Moreover, certain prior processes require one or more dehydrohalogenation steps, and it is not uncommon that a significant amount of waste is produced as a result of such steps.

In view of the above and other failures of the prior art, applicants have come to appreciate a need for new processes for manufacturing fluorinated alkenes such as, for example, 3,3,3-trifluoropropene, particularly but not exclusively processes that use readily available starting materials, and/or that are more cost effective than certain prior processes, and/or that reduce the need to dispose of environmentally unfriendly waste products.

SUMMARY OF THE INVENTION

One aspect of the present invention provides methods of reducing the emission of environmentally detrimental compounds from a process that produces as a byproduct a compound of formula (I) $R_f—C(R_1)=C(R_2)H$ wherein $R_f$ is fluorine or a substituted or unsubstituted $C_1–C_{20}$ straight or branched-chain fluorinated alkyl, and $R_1$ and $R_2$ are independently H, Cl, Br, or I, provided that at least one of $R_1$ or $R_2$ is Cl, Br, or I. In preferred aspects the method comprises reacting the fluorohaloalkene of formula (I) with a formate salt, preferably in the presence of palladium catalyst, to produce at least one fluoroalkene having a lower degree of chlorination, bromination or iodination than said compound of formula (I). In certain preferred embodiments, the methods comprise separating at least a portion of any unreacted compound of formula (I) from the reaction product and then exposing said separated compound to said reaction step, for example by recycling unreacted fluorohaloalkene of formula (I) to a reactor in which the reaction step is carried out.

In another aspect, the present invention provides methods for producing a fluoroalkene of the formula (II) $R_f—CH=CH_2$ from a fluorohaloalkene having formula (I) $R_f—C(R_1)=C(R_2)H$, wherein $R_f$ is fluorine or a substituted or unsubstituted $C_1–C_{20}$ straight or branched-chain fluorinated alkyl, and $R_1$ and $R_2$ are independently H, Cl, Br, or I, provided that at least one of $R_1$ or $R_2$ is Cl, Br, or I. In this aspect the methods comprise providing a compound of formula (I) and contacting the fluorohaloalkene of formula (I) with formate salt, preferably in the presence of catalyst, to reduce the Cl, Br or I atom of said compound and produce a compound of formula (II).

DETAILED DESCRIPTION OF THE INVENTION

Figure 1:
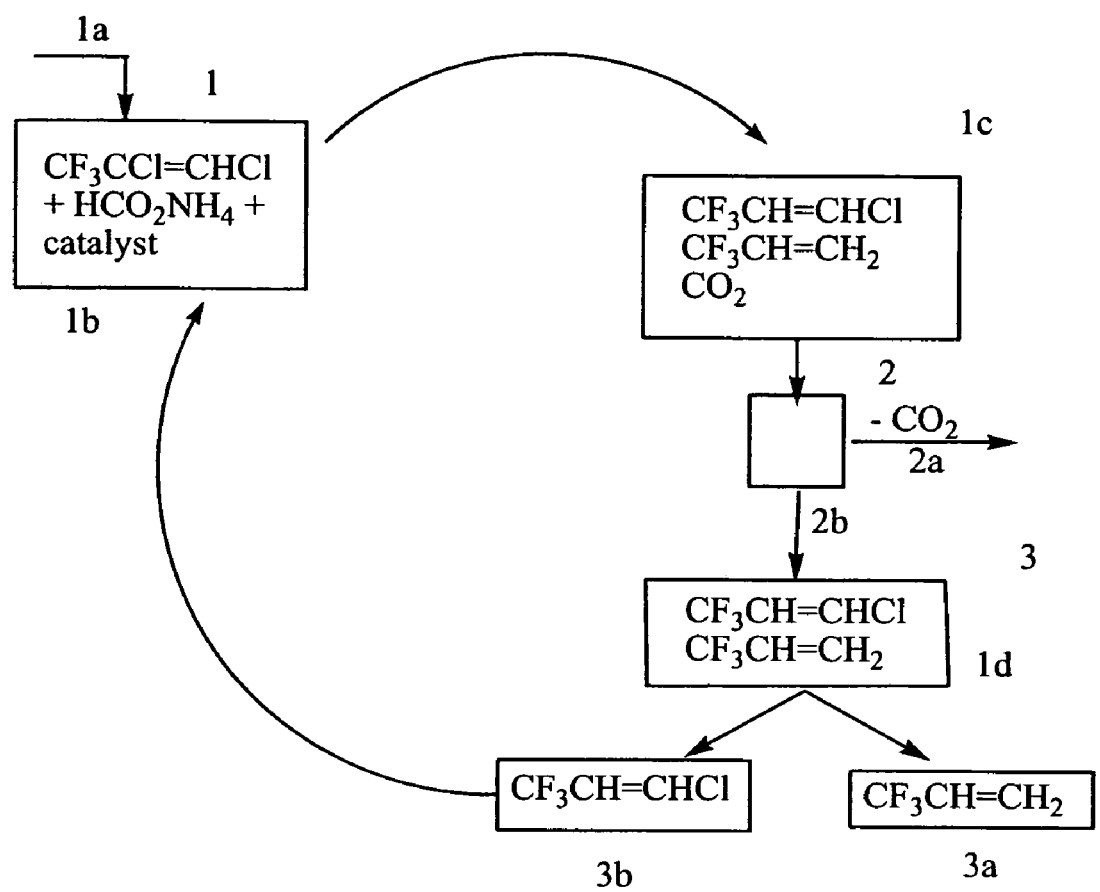
FIG. 1 is a diagram of a process according to certain preferred embodiments of the present invention.

The term "$C_1$–$C_{20}$ alkyl," as used herein, refers to saturated, straight- or branched-chain hydrocarbon radicals containing between 1 and 20 carbon atoms, respectively. Examples of $C_1$–$C_2$ alkyl radicals include, but are not limited to, methyl, ethyl, propyl, isopropyl, n-butyl, tertbutyl, neopentyl, n-hexyl, octyl, decyl, and dodecyl radicals.

The terms "halo" and "halogen," as used herein, refer to an atom selected from chlorine, bromine and iodine.

The terms "alkene" or "alkenyl," as used herein, denote a monovalent group derived from a hydrocarbon moiety having at least one carbon—carbon double bond. Alkenyl groups include, but are not limited to, for example, ethenyl, propenyl, butenyl, 1-methyl-2-buten-1-yl, and the like.

The term "fluorohaloalkene" denotes an alkene group, as defined above having, in addition to at least one fluorine atom, one or more additional halogen atoms attached thereto, and is exemplified by such groups as fluorochloromethyl, fluorobromoethyl, and the like.

The term "substituted," as used herein to refer to a straight or branched-chain fluorinated alkyl group refers to substitution by independent replacement of one or more hydrogen atoms of the alkyl group with, for example, F, Cl, Br, I, OH, $NO_2$, CN, $C_1$–$C_6$-alkyl, C(O)-aryl, C(O)-heteroaryl, methoxy, methoxyethoxy, amino, benzylamino, arylamino, heteroarylamino, methylthiomethyl, and the like.

Preferred aspects of the present invention provide an advantageously simple process for producing a desirable fluoroalkene of the formula (II) $R_f$—CH=$CH_2$ from a relatively undesirable fluorohaloalkene of formula (I):

$$R_f-C(R_1)=C(R_2)H \qquad (I)$$

wherein in each of formulas (I) and (II) $R_f$ is fluorine or a substituted or unsubstituted $C_1$–$C_{20}$ straight or branched-chain fluorinated alkyl, and $R_1$ and $R_2$ are independently H, Cl, Br, or I, provided that at least one of $R_1$ or $R_2$ is Cl, Br, or I. An important step in the preferred methods is reacting the fluorohaloalkene of formula (I) by contacting it with a hydrogen-donor reducing agent such as, for example, a formate-containing reducing agent, preferably in the presence of a catalyst. Hydrogen-donor reducing agents useful according to the present invention are exemplified in, for example, *J. Org. Chem.* 1995, 60, 1347–1355.

In the formulas (I) and (II) above, $R_f$ as a substituted or unsubstituted $C_1$–$C_{20}$ straight or branched-chain fluorinated alkyl typically may be, for example, fluoromethyl, difluoromethyl, trifluoromethyl, fluoroethyl, difluoroethyl, trifluoroethyl, pentafluoroethyl, perfluoropropyl, perfluorobutyl, perfluoropentyl, perfluorohexyl, and the like. In certain preferred embodiments, $R_f$ is trifluoromethyl.

In a preferred embodiment, the reacting step of the present invention comprises selectively reducing one or more fluorohaloalkenes such as, for example, 1,2-dichloro-3,3,3-trifluoropropene ($CF_3CCl$=CHCl; HCFC 1223), 1-chloro-3,3,3-trifluoropropene ($CF_3CH$=CHCl; HCFC 1233), or mixtures thereof to one or more fluoroalkenes having a lower degree of chlorination, bromination and/or iodination, which in many cases are more desirable than the starting compounds of formula (I). In certain preferred embodiments, the preferred fluoroalkene produced in accordance with the present invention comprises, for example, trifluoropropene, and even more preferably 3,3,3-trifluoropropene ($CF_3CH$=$CH_2$; 333-TFP).

Two preferred embodiments of the invention are illustrated schematically in Schemes I and II.

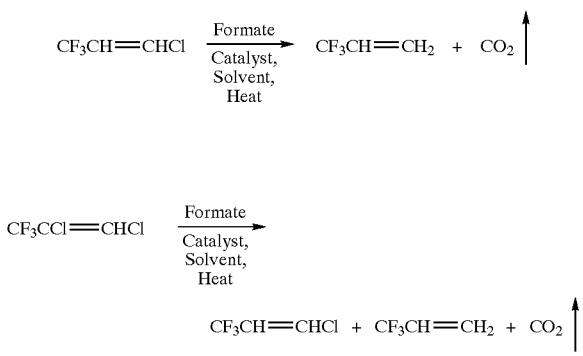

Referring to Schemes I and II, 1-chloro-3,3,3-trifluoropropene ($CF_3CH$=CHCl; HCFC 1233) and 1,2-dichloro-3,3,3-trifluorpropene ($CF_3CCl$=CHCl; HCFC 1223) are preferred because they are readily available and, moreover, because these compounds are frequently present as unwanted byproducts in waste streams that would otherwise have to be disposed of at additional cost or with the result of undesirable environmental consequences. As described in European Patent No. EP 0 931 043 B1, for example, 1,2-dichloro-3,3,3-trifluorpropene ($CF_3CCl$=CHCl; HCFC 1223) (Scheme II) is a by-product formed in the manufacture of 1,1,1,3,3-pentafluoropropane ($CF_3CH_2CF_2H$; HFC 245fa) by Honeywell International, Inc. (Morristown, N.J.). Such by-product is typically produced in large quantities and has heretofore frequently been treated as waste and incinerated. Accordingly, in certain preferred embodiments, the present invention provides methods for reducing pollution from a process that produces as a byproduct a compound of formula (I):

$$R_f-C(R_1)=C(R_2)H \qquad (I)$$

wherein $R_f$ is fluorine or substituted or unsubstituted $C_1$–$C_{20}$ straight or branched-chain fluorinated alkyl, and $R_1$ and $R_2$ are independently H, Cl, Br, or I, provided that at least one of $R_1$ or $R_2$ is Cl, Br, or I. In a more preferred embodiment of the present invention, waste by-product such as, for example, 1,2-dichloro-3,3,3-trifluorpropene ($CF_3CCl$=CHCl; HCFC 1223) is converted into useful compounds such as, for example, 3,3,3-trifluoropropene ($CF_3CH$=$CH_2$).

In other preferred embodiments of the invention, fluorohaloalkenes that are suitable for use as starting materials in the methods of the present invention include, for example, fluorochloroalkenes such as, for example, 1,2-dichloro-4,4,4-trifluorbutene ($CF_3CH_2CCl$=CHCl), 1-chloro-4,4,4-trifluorobutene ($CF_3CH_2CH$=CHCl), 1,2-dichloro-5,5,5-trifluorpentene ($CF_3CH_2$ $CH_2CCl$=CHCl), 1-chloro-5,5,5-trifluoropentene ($CF_3CH_2$ $CH_2CH$=CHCl), and mixtures thereof.

Preferably, the starting material of the illustrated Scheme I, 1-chloro-3,3,3-trifluorpropene ($CF_3CH$=CHCl; HCFC 1233), is an intermediate formed in the manufacture of 1,1,1,3,3-pentafluoropropane ($CF_3CH_2CF_2H$; HFC 245fa). Such process is described, for example, in European Patent No. EP 0 931 043 B 1, assigned to Honeywell International, Inc. (Morristown, N.J.), which is the assignee of the present invention. Both 1,2-dichloro-3,3,3-trifluorpropene ($CF_3CCl$=CHCl; HCFC 1223) and 1-chloro-3,3,3-trifluoropropene ($CF_3CH=CHCl$; HCFC 1233) are also commercially available from, for example, Synquest Laboratory (Alachua, Fla.).

It is contemplated that the methods of the present invention are adaptable for use with any one of the well known formate-based reducing agents, and all such reducing agents are within the scope of the present invention. In certain embodiments, it is preferred to use a formate salt as the reducing. In certain preferred embodiments the formate salt comprises and/or is selected from the group consisting of sodium formate, potassium formate, lithium formate, cesium formate, ammonium formate, triethylamonium formate, and mixtures of two or more thereof. The reducing agent/hydrogen donor according to the present invention preferably comprises, and in certain embodiments consists essentially of, ammonium formate. Ammonium formate is known for use as a reducing agent when, for example, a molecule has multiple or labile moieties (see Ram et. al., *Synthesis* (1988), 91–95).

It is also contemplated that a wide variety of catalysts are adaptable for use with the present invention in view of the teachings contained herein, including those catalysts that are known to those skilled in the art to be used as catalysts in reduction reactions. In certain preferred embodiments, the catalyst used in accordance with the present methods comprises a rhodium based catalyst. In certain more preferred embodiments, the catalyst used in accordance with the present methods comprises a palladium-based catalyst. Exemplary palladium-based catalysts suitable for use in the invention include, for example, Pd/C, $PdCl_2(PPh_3)_2$, tris(dibenzlideneacetone)dipalladium(0), $Pd_2(dba)_3$, tris(dibenzlideneacetone)dipalladium(0) chloroform complex, $Pd_2(dba)_3$—$CHCl_3$, tetrakis(triphenylphosphine)palladium(0), $Pd(PPh_3)_4$, and mixtures thereof. In certain highly preferred embodiments, the catalyst comprises, or consists essentially of, $Pd(PPh_3)_4$ and $Pd_2(dba)_3$.

The reaction step of the present invention preferably comprises a reaction which occurs in the presence of a liquid solvent, although it will be appreciated that other reaction conditions are adaptable for use within the scope of the present invention. For solvent based reactions, it is preferred that the reaction comprise providing a solvent medium comprising one or more ethereal solvents. Exemplary ethereal solvents include, for example, tetrahydrofuran (THF), acetonitrile, diethyl ether, diglyme, monoglyme, dioxane, and mixtures thereof. In certain preferred embodiments, the solvent comprises or consists essentially of tetrahydrofuran.

In other embodiments of the invention, solvents such as, for example, alcohols, and dimethylformamide can be employed.

Reactions according to the present invention are preferably conducted in closed reaction vessels such as, for example, an autoclave, however, employment of an open reaction vessel is also contemplated under certain conditions. It will be appreciated by those skilled in the art that the volatility of the starting materials will, in part, determine whether an open or closed reaction vessel is employed. It will also be appreciated by those skilled in the art that the volatility of the fluorohaloalkene starting materials will depend upon, for example, the number of carbon atoms contained therein. For example, one skilled in the art will typically have more freedom to use an open reaction vessel with a high-boiling fluorohaloalkene starting material of formula (I) $R_f$—$C(R_1)=C(R_2)H$ as defined above where, for example, $R_f$ is a fluorinated alkyl group having 10 carbons, than with a lower-boiling fluorochloroalkene staring material according to the invention such as, for example, where $R_f$ is a trifluoromethyl group.

In preferred embodiments of the invention, the reactions of the present invention are conducted in closed reaction systems. The reaction systems may comprise any apparatus or combination of apparatus suitable for use in conducting a reaction according to the present invention.

Those skilled in the art will appreciate that the conditions under which the present reaction occurs, including the pressure, temperature and period of reaction, will depend on numerous factors, including the particular starting reagents used and the desired reaction yield. The reactions of the present invention thus may be conducted under any suitable temperature, pressure, reaction time, and like conditions, as noted above. In preferred embodiments, the present reactions are conducted under ambient/autogenous pressure conditions. In certain preferred embodiments, the reaction temperature is from about 25° C. to about 150° C., and even more preferably from about 80° C. to about 120° C. Reaction temperatures as described below in the Examples are also preferred in certain embodiments. The reactions of the present invention may be conducted for any suitable length of time. In certain preferred embodiments, the reaction time is preferably about 36 hours or less, and more preferably about 24 hours or less.

It is contemplated that the reaction step of the present invention may be carried using a wide variety of techniques generally known in the art, including the use of batchwise, continuous and semi-continuous processes. In certain preferred embodiments of the invention, the reactions of the present invention are conducted in a continuous process. One preferred continuous process is illustrated by FIG. 1 and is described below.

Referring now to FIG. 1, in step 1 of the illustrated embodiment, a fluorohaloalkene of formula (I), such as, for example, 1,2-dichloro-3,3,3-trifluorpropene ($CF_3CCl=CHCl$; HCFC 1223), is contained in a process stream 1*a* and is introduced to a reactor 1*b* along with a reducing agent, such as an ammonium formate reducing agent, and a suitable catalyst such as, for example, those described above. The reaction is allowed to proceed as detailed in the Examples below.

In a preferred embodiment, the fluorochloroalkene 1,2-dichloro-3,3,3-trifluorpropene ($CF_3CCl=CHCl$; HCFC 1223), is included in a waste by-product stream from one or more other unit operations such as, for example, those described in European Patent No. EP 0 931 043 B 1. The reactor 1*b* is preferably a closed vessel such as, for example, an autoclave or a Parr® reactor.

In preferred embodiments of the invention, a crude reaction product stream 1*c* is produced and generally comprises unreacted starting materials as well as the desired fluorinated alkenes. Carbon dioxide, as well as other byproducts, may also be contained in the reaction product stream in minor quantities. Reaction product stream 1*c* typically is treated by introducing the stream to a carbon dioxide removal step 2 in which at least a portion of the carbon dioxide is separated and withdrawn as stream 2*a*. Removal of carbon dioxide may achieved, for example, by passing the reaction product stream, or some substream derived therefrom, through a cold trap maintained at a temperature of from about −50 to about −70° C. The next step in the process illustrated by FIG. 1, the substantially free carbon dioxide reaction product stream 2*b* is introduced into a separation step 3. According to preferred embodiments of the invention, the separation step comprises one or more distillation stages, preferably a multistage distillation column. In this illustrated embodiment, for example, the $CF_3CH=CH_2$ (boiling point −20° C.) and $CF_3CH=CHCl$ (boiling point 19° C.) are contained in the stream 1*d* and are readily separated by distillation. In preferred embodiments, separated $CF_3CH=CHCl$ is recycled in stream 3*b* to the reaction step 1 and the product stream 3*a* containing the desired fluoroalkene, such as $CF_3CH=CH_2$, is sent to further processing or to storage.

It will be appreciated by those skilled in the art that the fluorohaloalkene starting materials of the present invention are widely recognized as pollutants that are harmful to the Earth's ozone layer. Accordingly, it will be appreciated that another aspect of the present invention is a method of reducing pollution from a process that produces as a byproduct a compound of formula (I) $R_f$—$C(R_1)$=$C(R_2)H$ wherein $R_f$ is fluorine or a substituted or unsubstituted $C_1$–$C_{20}$ straight or branched-chain fluorinated alkyl, and $R_1$ and $R_2$ are independently H, Cl, Br, or I, provided that at least one of $R_1$ or $R_2$ is Cl, Br, or I. In one preferred embodiment of this aspect of the invention, the present methods comprise providing to a reactor a fluorohaloalkene waste by-product stream, which in certain preferred embodiments comprise the effluent from one or more other unit processes that otherwise would have been transferred to a waste treatment operation, such as incineration, and reducing the fluorohaloalkene according to the invention as described above.

The following examples are presented for the purpose of illustrating the forgoing description and are not meant to limit the scope of the claimed invention.

EXAMPLES

Example 1

Conversion of $CF_3$—CH=CHCl (HCFC 1233) to $CF_3CH$=$CH_2$ (HFC 1243) with $PdP(Ph_3)_4$ Catalyst A 250 mL Parr Reactor/autoclave was charged with 30 mL tetrahydrofuran to which 0.5 grams (0.04 mmol) [tetrakis(triphenylphosphine)palladium(0), $[Pd(PPh_3)_4]$, 10.0 grams of ammonium formate (158 mmol), and 10.0 grams cold (5–10° C.) $CF_3CH$=CHCl (77 mmol) were added under nitrogen. The reactor was sealed immediately, cooled to −30 to −40° C., and partially evacuated. The contents in the Parr reactor were brought to room temperature and gradually heated to 100° C. with stirring. The reactants were maintained at this temperature for 24 hours. During this time, the pressure in the reactor increased to approximately 180–200 psi. The reactor was then cooled to 25° C. and the volatile materials were collected in an evacuated metal cylinder.

Gas chromatographic (GC) analysis of the volatile materials indicated $CF_3CH$=$CH_2$ as the main product with trace amounts of $CF_3CH$=CHCl and carbon dioxide. The reaction mixture was cooled to 0° C. and filtrate was analyzed by gas chromatograph (GC) which indicated approximately a 40% conversion of $CF_3CH$=CHCl to $CF_3CH$=$CH_2$. GC/MS (EI mode) of volatiles: m/e at 96 $M^+$ for $CF_3CH$=$CH_2$. Identity of $CF_3CH$=$CH_2$ was confirmed by comparison with a known sample. Purification of the product can be accomplished by passing the product through a cold trap (to remove $CO_2$ and unreacted starting material at about −70° C.) and distillation.

Example 2

Conversion of $CF_3$—CH=CHCl (HCFC 1233) to $CF_3CH$=$CH_2$ (HFC 1243) with $Pd_2(dba)_3$ Catalyst A 250 mL Parr Reactor/autoclave was charged with 30 mL tetrahydrofuran (30 mL) to which 0.456 grams of tris(dibenzlideneacetone)dipalladium(0), $Pd_2(dba)_3$ (2.0 mmol), 0.8 grams of tributyl phosphine (2.0 mmol), 8.0 grams of ammonium formate (126 mmol), and 10.0 grams of cold (5–10° C.) $CF_3CH$=CHCl (77 mmol) were added under nitrogen. The reactor was sealed immediately, cooled to −30 to −40° C., and partially evacuated. The contents in the Parr reactor were brought to room temperature, gradually heated to 100° C. with stirring. The reactants were maintained at this temperature for 24 hours during which the internal pressure rose to approximately 200 PSI. The reactor was then cooled to 25° C. and the volatile materials were passed through a trap at 70–78° C. and collected in a cold evacuated metal cylinder. Gas chromatographic (GC) analysis of the volatile materials collected indicated $CF_3CH$=$CH_2$ as the main product with trace amounts of $CF_3CH$=CHCl and carbon dioxide. The reaction mixture was cooled to 0° C. and filtrate was analyzed by GC which indicated approximately a 35% conversion of $CF_3CH$=CHCl to $CF_3CH$=$CH_2$.

GC/MS (EI mode) of volatiles: m/e at 96 $M^+$ for $CF_3CH$=$CH_2$.

It is noteworthy that the above reaction was repeated, except that dioxane was substituted for tetrahydrafuran as the solvent. The result was essentially the same.

Example 3

Conversion of $CF_3$—CH=CHCl (HCFC 1233) to $CF_3CH$=$CH_2$(HFC 1243) with $Pd_2(dba)_3 \cdot CHCl_3$ Catalyst The reaction was carried out as in Example 2 except that an equivalent amount of catalyst $Pd_2(dba)_3$ was substituted by tris(dibenzlideneacetone)dipalladium(0)chloroform complex, $Pd_2(dba)_3 \cdot CHCl_3$. The extent of conversion of HCFC 1233 to $CF_3CH$=$CH_2$ was essentially the same as in Example 2.

Example 4

Conversion of $CF_3$—CCl=CHCl (HCFC 1223) to $CF_3CH$=$CH_2$ (HFC 1243) with $Pd(Ph_3)_4$ Catalyst in Tetrahydrofuran A 250 mL Parr Reactor/autoclave was charged with 30 mL of tetrahydrofuran to which 0.5 grams of tetrakis(triphenylphosphine)palladium(0), $Pd(Ph_3)_4$ (0.04 mmol), 10 grams of ammonium formate (158 mmol), and 10 grams of $CF_3CCl$=CHCl (61 mmol) were added under nitrogen. The reactor was sealed immediately, cooled to −30 to −40° C., and partially evacuated. The contents in the Parr reactor were brought to room temperature and gradually heated to 100° C. with constant stirring. The reactants were maintained at this temperature for 24 hours. The reactor was then cooled to 25° C. and the volatile materials were collected in an evacuated metal cylinder. Gas chromatographic (GC) analysis of the volatile materials indicated that $CF_3CH$=$CH_2$ and $CF_3CH$=CHCl were present at a ratio of about 57:42. Carbon dioxide was also present. The reaction mixture was cooled to 0° C. and filtered under pressure, the filtrate was analyzed by GC which indicated about a 40% conversion of $CF_3CCl$=CHCl to $CF_3CH$=CHCl and $CF_3CH$=$CH_2$.

GC/MS (EI mode) of volatiles: m/e at 96 $M^+$ for $CF_3CH$=$CH_2$ and m/e at 130/132 for $CF_3CH$=CHCl (for $^{35}Cl/^{37}Cl$ isotopes).

Example 5

Conversion of $CF_3$—CCl=CHCl (HCFC 1223) to $CF_3CH$=$CH_2$ (HFC 1243) with $Pd_2(dba)_3$ Catalyst A 250 mL Parr Reactor/autoclave was charged with 30 mL of tetrahydrofuran to which 0.45 grams of tris(dibenzlideneacetone)dipalladium(0), Pd$_2$(dba)$_3$ (2.0 mmol), 8.0 grams of ammonium formate (126 mmol), 0.8 grams of tri(butyl)phosphine (2.0 mmol), and 10.0 grams of CF$_3$CCl=CHCl (61 mmol) were added under nitrogen. The reactor was sealed immediately, cooled to −30 to −40° C., and partially evacuated. The contents in the Parr reactor were brought to room temperature, gradually heated to 100° C. with stirring. The reactants were maintained at this temperature for 24 hours. The reactor was then cooled to 25° C. and the volatile materials were collected in an evacuated metal cylinder. Gas chromatographic (GC) analysis of the volatile materials indicated the presence of CF$_3$CH=CH$_2$ and CF$_3$CH=CHCl in the ratio of about 6:4. Carbon dioxide was also present. The reaction mixture was cooled to 0° C. and filtered under pressure, the filtrate was analyzed by GC which indicated about a 30% conversion of CF$_3$CCl=CHCl to CF$_3$CH=CHCl and CF$_3$CH=CH$_2$.

GC/MS (EI mode) of volatiles: m/e at 96 M$^+$ for CF$_3$CH=CH$_2$ and m/e at 130/132 for CF$_3$CH=CHCl (for $^{35}$Cl/$^{37}$Cl isotopes).

The reaction was also conducted the same way as described above, except that dioxane was substituted for tetrahydrafuran as the solvent. The result was essentially the same.

Example 6

Conversion of CF$_3$—CCl=CHCl (HCFC 1223) to CF$_3$CH=CH$_2$ (HFC 1243) with Pd$_2$(dba)$_3$.CHCl$_3$ Catalyst The reaction was carried out as in Example 5 except that an equivalent amount of catalyst Pd$_2$(dba)$_3$ was substituted by tris(dibenzlideneacetone)dipalladium(0)chloroform complex, Pd$_2$(dba)$_3$.CHCl$_3$. The extent of conversion of CF$_3$CCl=CHCl to CF$_3$CH=CHCl and CF$_3$CH=CH$_2$ was essentially the same as in Example 4.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

What is claimed is:

1. A method of reducing environmentally undesirable emissions from a process that produces as a byproduct a chlorinated compound of formula (I)

wherein
R$_f$ is fluorine or substituted or unsubstituted C$_1$–C$_{20}$ straight or branched-chain fluorinated alkyl; and
R$_1$ and R$_2$ are independently H, Cl, Br, or I, provided that at least one of R$_1$ or R$_2$ is Cl, the method comprising the steps of:
providing a waste by-product containing at least one compound of formula (I);
exposing said waste by-product to reaction conditions effective to reduce at least a substantial portion of the compound of formula (I) contained in said waste by-product to at least one fluoroalkene having a lower degree of chlorination than said compound of formula (I) by contacting said waste by-product with at least one formate salt in the presence of a catalyst, said exposing step producing a reaction product stream comprising compound of formula (I) and said at least one fluoroalkene;
separating at least a portion of said at least one fluoroalkene produced in said exposing step from said reaction product stream to produce a stream relatively rich in said compound of formula (I); and
subjecting said stream relatively rich in the compound of formula (I) to said exposing step.

2. The method of claim 1 wherein the waste by-product is selected from the group consisting of 1,2-dichloro-3,3,3-trifluorpropene, 1-chloro-3,3,3-trifluorpropene, and mixtures thereof.

3. The method of claim 2 wherein the waste by-product is 1,2-dichloro-3,3,3-trifluorpropene.

4. The method of claim 1 wherein the reducing step is carried out in an ethereal solvent.

5. The method of claim 4 wherein the ethereal solvent is dioxane, tetrahydrofuran, or mixtures thereof.

6. The method of claim 5 wherein the ethereal solvent is tetrahydrofuran.

7. The method of claim 1 wherein the formate salt is selected from the group consisting of sodium formate, potassium formate, lithium formate, cesium formate, ammonium formate, triethylammonium formate, and mixtures thereof.

8. The method of claim 7 wherein the formate salt is ammonium formate.

9. The method of claim 1 wherein the catalyst is a palladium catalyst selected from the group consisting of tris(dibenzlideneacetone)dipalladium(0), Pd$_2$(dba)$_3$, tris(dibenzlideneacetone)dipalladium(0)chloroform complex, Pd$_2$(dba)$_3$—CHCl$_3$ or tetrakis(triphenylphosphine)palladium(0), Pd(PPh$_3$)$_4$, and mixtures thereof.

10. The method of claim 9 wherein the palladium catalyst is Pd(PPh$_3$)$_4$.

11. The method of claim 10 wherein the palladium catalyst is Pd$_2$(dba)$_3$.

12. The method of claim 1 wherein the formate salt is ammonium formate; and the catalyst is selected from the group consisting of Pd(PPh$_3$)$_4$ and Pd$_2$(dba)$_3$.

13. A method for producing a fluoroalkene of the formula R$_f$—CH=CH$_2$ from a fluorohaloalkene of formula (I)

wherein
R$_f$ is fluorine or a substituted or unsubstituted C$_1$–C$_{20}$ straight or branched-chain fluorinated alkyl; and
R$_1$ and R$_2$ are independently H, Cl, Br, or I, provided that at least one of R$_1$ or R$_2$ is Cl, Br, or I, comprising the steps of:
contacting the fluorohaloalkene with at least one formate salt in the presence of a catalyst.

14. The method of claim 13 wherein the fluorohaloalkene is selected from the group consisting of 1,2-dichloro-3,3,3-trifluorpropene, 1-chloro-3,3,3-trifluorpropene, and mixtures thereof.

15. The method of claim 14 wherein the fluorohaloalkene is 1,2-dichloro-3,3,3-trifluorpropene.

16. The method of claim 13 wherein the contacting step is carried out in an ethereal solvent.

17. The method of claim 16 wherein the ethereal solvent is dioxane, tetrahydrofuran, or mixtures thereof.

18. The method of claim 17 wherein the ethereal solvent is tetrahydrofuran.

19. The method of claim 13 wherein the formate salt is selected from the group consisting of sodium formate, potassium formate, lithium formate, cesium formate, ammonium formate, triethylamonium formate, and mixtures thereof.

20. The method of claim 19 wherein the formate salt is ammonium formate.

21. The method of claim 13 wherein the catalyst is a palladium catalyst selected from the group consisting of tris(dibenzlideneacetone)dipalladium(0), $Pd_2(dba)_3$, tris(dibenzlideneacetone)dipalladium(0)chloroform complex, $Pd_2(dba)_3 \cdot CHCl_3$ or tetrakis(triphenylphosphine)palladium(0), $Pd(PPh_3)_4$, and mixtures thereof.

22. The method of claim 21 wherein the palladium catalyst is $Pd(PPh_3)_4$.

23. The method of claim 21 wherein the palladium catalyst is $Pd_2(dba)_3$.

24. The method of claim 13 wherein the formate salt is ammonium formate; and the catalyst is selected from the group consisting of $Pd(PPh_3)_4$ and $Pd_2(dba)_3$.

25. A method for continuous production of 3,3,3-trifluoropropene comprising:
   providing a fluorochloroalkene selected from the group consisting of 1,2-dichloro-3,3,3-trifluorpropene, 1-chloro-3,3,3-trifluorpropene, and mixtures thereof;
   contacting the fluorochloroalkene with at least one formate salt and a catalyst;
   separating 3,3,3-trifluoropropene from any unreacted fluorochloroalkene; and
   recycling the unreacted fluorochloroalkene to the reactor.

26. The method of claim 25 wherein the reaction is carried out in an ethereal solvent.

27. The method of claim 26 wherein the ethereal solvent is dioxane, tetrahydrofuran, or mixtures thereof.

28. The method of claim 25 wherein the ethereal solvent is tetrahydrofuran.

29. The method of claim 25 wherein the formate salt is selected from the group consisting of sodium formate, potassium formate, lithium formate, cesium formate, ammonium formate, triethylamonium formate, and mixtures thereof.

30. The method of claim 25 wherein the catalyst is a palladium catalyst selected from the group consisting of tris(dibenzlideneacetone)dipalladium(0), $Pd_2(dba)_3$, tris(dibenzlideneacetone)dipalladium(0)chloroform complex, $Pd_2(dba)_3 \cdot CHCl_3$ or tetrakis(triphenylphosphine)palladium(0), $Pd(PPh_3)_4$, and mixtures thereof.

31. The method of claim 30 wherein the palladium catalyst is $Pd(PPh_3)_4$.

32. The method of claim 30 wherein the palladium catalyst is $Pd_2(dba)_3$.

33. The method of claim 25 wherein the formate salt is ammonium formate; and the catalyst is selected from the group consisting of $Pd(PPh_3)_4$ and $Pd_2(dba)_3$.

34. The method of claim 25 wherein the separating step is performed by distillation.

35. The method of claim 25 further comprising the step of removing carbon dioxide prior to the separating step.

36. The method of claim 25 wherein the providing step comprises generating a byproduct stream of fluorochloroalkenes selected from the group consisting of 1,2-dichloro-3,3,3-trifluorpropene, 1-chloro-3,3,3-trifluorpropene, and mixtures thereof.

37. The method of claim 36 wherein the providing step comprises generating a byproduct stream of 1,2-dichloro-3,3,3-trifluoropropene.

* * * * *